United States Patent [19]

Knopick et al.

[11] 4,164,941

[45] Aug. 21, 1979

[54] DISPOSABLE DRAPE FOR SURGICAL TABLE

[75] Inventors: Robert A. Knopick, Downers Grove; Allen B. Morlock, Naperville, both of Ill.

[73] Assignee: Steraplast, Inc., Bensenville, Ill.

[21] Appl. No.: 852,692

[22] Filed: Nov. 18, 1977

[51] Int. Cl.² ............................................. A61B 19/06
[52] U.S. Cl. ............................................... 128/132 D
[58] Field of Search ............... 128/132 D, 132 R, 292; 206/440

[56] References Cited

U.S. PATENT DOCUMENTS

| | | | |
|---|---|---|---|
| 3,537,446 | 11/1970 | Rowland, Jr. et al. | 206/440 X |
| 3,856,006 | 12/1974 | Krzewinski | 128/132 D |
| 4,027,665 | 6/1977 | Scrivens | 128/132 D |

*Primary Examiner*—Henry J. Recla
*Attorney, Agent, or Firm*—Robert E. Wagner; Gerald T. Shekleton; Leo J. Aubel

[57] ABSTRACT

A disposable drape for a surgical overhead table; the drape is liquid-proof and covers the entire surface of the associated table. Also, the drape is of a construction which will prevent the passage of any bacteria through the surface area of the drape.

1 Claim, 7 Drawing Figures

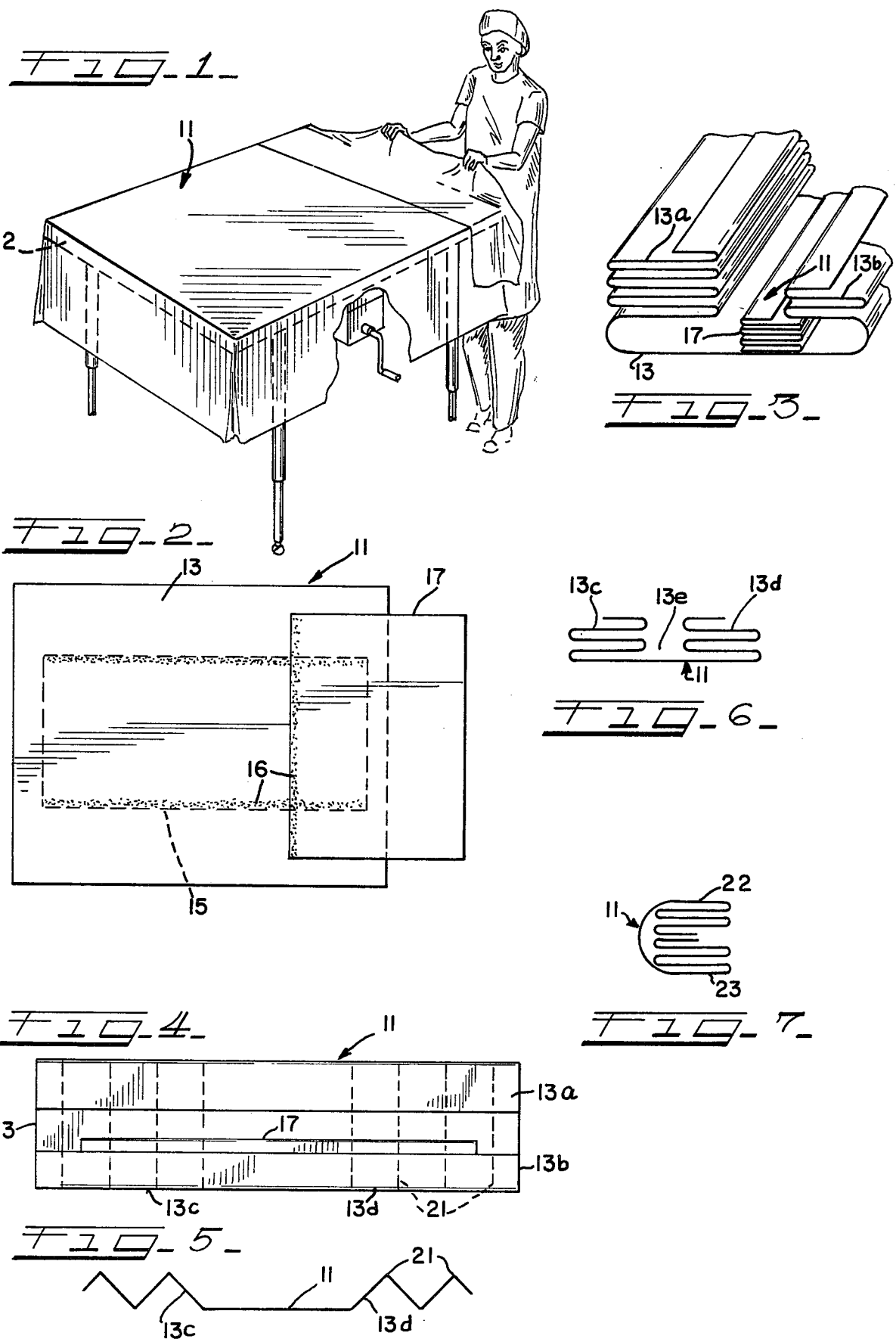

4,164,941

DISPOSABLE DRAPE FOR SURGICAL TABLE

BACKGROUND OF THE INVENTION

Drapes, for use with surgical operating room tables, of various constructions and of various materials are known in the art. Such prior art drapes made of material fibers, or of chemically derived fibers, and of various sizes for use on surgical tables, are well known; note for example, the fiber Kasel ® made by the Kimberly Clark Co.

While such prior art drapes are generally satisfactory, it is a specific object of the present invention to provide an improved surgical table drape which is totally fluid-proof and covers the entire area of an overhead surgical table.

Another object of the present invention is to provide a surgical drape which provides full coverage over the sides of the overhead surgical tables.

Still another object of the present invention is to provide a disposable surgical drape which is constructed of materials which permit sterilization thereof during its manufacture.

The foregoing and other objects, features and advantages of the invention will be apparent from the following more particular description of a preferred embodiment of the invention, as illustrated in the accompanying drawings, wherein:

DESCRIPTION OF THE DRAWINGS

FIG. 1 is an isometric view showing the use of the inventive drape as positioned over a surgical table;

FIG. 2 is a plan view of the inventive drape with an extension sheet bonded to a base sheet in accordance with the invention, and indicating the plastic film adhered to the base sheet; and, FIGS. 3, 4, 5, 6 and 7 shows a preferred fold configuration of the drape of FIG. 2.

DESCRIPTION OF THE INVENTION

Referring first to FIGS. 1 and 2, the inventive disposable drape 11 for overhead surgical tables 12 comprises a base sheet 13 of a cellulose material such as of the fabric manufactured and sold by the Kimberly Clark Co. under the trademark Kacel ®. In one embodiment, the base sheet 13 is of such a fabric comprising a three-ply sheet with nylon scrim, and the sheet is treated for fluid repellency. In one embodiment, the sheet 13 is of rectangular shape with dimensions of 84 inches by 77 inches, such as to cover a table surface measuring approximately 48 inches by 34 inches. Thus, the base sheet 13 is sufficiently large to cover the entire surface area of the associated surgical table and a drape substantially over the sides of the table 12. It will of course be understood that although various dimensions are stated in detail that the invention or its concept is not limited to these dimensions.

A plastic film 15 is bonded by a suitable adhesive 16 to one surface of the base sheet 13, and at a central position on the base sheet 13. In the embodiment mentioned, film 15 is rectangular in shape with dimensions of 75 inches by 45 inches. The adhesive utilized to bond the film, indicated in FIG. 2 by the speckled shading, is of a suitable commercially available adhesive such as that manufactured by the H. B. Fuller Co. as Fullers Adhesive R-3168-EB. The film 15 is impervious to fluid, that is, it is fluid-proof and may be of a 1.5 to 2 mil thickness polyethylene, polypropelene, polyvinylchloride, or polyethylene methacrylate copolymer film. It is, of course, important that the film 15 possess antistatic properties. The film 15 is of sufficient size to cover the horizontal surface of the associated table 12 such that the overall drape 11 provides totally fluid-proof area on the portion of the drape placed on the horizontal surface of the table.

The drape 11 includes an extension sheet 17 of the same material as the base sheet 13; and, in the aforesaid embodiment, the extension sheet 17 is 60 inches by 44 inches in size. The extension sheet 17 is bonded with adhesive 16 along an edge of its 60 inch dimension at a position toward the side of the base sheet 13 such that about one-half, or about 22 inches, of the extension sheet 17 extends outwardly from the edge of the base sheet 13 as indicated in FIG. 2.

The materials which comprise the base sheet 13, the plastic film 15 and the extension sheet 17 remain stable up to a sufficiently high temperature to permit sterilization of the drape 11 as is required during manufacture and assembly.

Importantly, the drape 11 comprising the extension sheet 17 adhesively bonded to the base sheet 13, provides an unbroken drape coverage from the associated table to the operating surface.

The drape 11 including the base sheet 13, the plastic film 15 and the extension sheet 17, thus provide an integral, or one piece, construction which is impervious to fluid and which will prevent the passage of bacteria through the surface area of the drape. Stated in a second way, the drape 11 provides an unbroken sterile field, including an extendable uncontaminated portion which can extend outwardly from the table surface.

The method or means of folding drape 11 such as for packaging, distribution and shipping, is shown in FIGS. 3, 4, 5, 6 and 7.

From the flat portion shown in FIG. 2, the drape 11 is first folded to a position as shown in FIG. 3. First, the extension sheet 17 is folded, starting from its adhered edge in an accordian or fan fold onto the base sheet 13. The base sheet 13 is in turn folded in double accordian folds as indicated by the reference numerals 13a and 13b. As can be clearly seen from FIG. 3, the first fold 13a extends to a position adjacent, but spaced from, the folded extension sheet 17; and the second fold 13b slightly overlaps the folded extension sheet 17.

Refer now to FIG. 4 which is, in essence, a top or plan view of the drawing of FIG. 3. After the drape 11 is in the folded position of FIGS. 3 and 4, the drape is folded in an accordian fold along the direction indicated by the lines 21 of FIG. 4 and FIG. 5. Next, the portions of the drape 11 indicated by the reference numerals 13c and 13d in FIGS. 4 and 5 are folded toward each other as shown in FIG. 6, to have a spacing 13e between the folded portions 13c and 13d. Finally, as shown in FIG. 7, portion 13c is folded over portion 13d and the drape 11 is ready for packaging.

As will be appreciated in order to place or position the drape 11 on the associated table 12, substantially a reverse procedure to unfold the folded drape is followed. For example, from the position shown in FIG. 7, the drape 11 can be placed on the associated table 12 and the drape unfolded. Note that the particular folding pattern permits the entire drape 11 to be conveniently unfolded and extended for use, by merely grasping the various free edge of the folds and pulling the folds outwardly from their folded position. The extension sheet 17 can also be conveniently unfolded for use, as indicated in FIG. 1, merely by grasping the free edge of the sheet 17 and pulling the edge outwardly.

While the invention has been particularly shown and described with reference to a preferred embodiment thereof, it will be understood by those skilled in the art that various changes in form and details may be made therein without departing from the spirit and scope of the invention.

We claim:

1. A disposable drape for covering a surgical table and providing drape coverage extending from the table to an operating surface, said drape comprising a compact package for transporting and handling thereof, said drape comprising a non-fenestrated base sheet adapted to lie directly over said table surface, a fluid impervious plastic film of smaller size than said base sheet bonded onto one surface of said base sheet and in a central portion of the base sheet for preventing fluid flow from penetrating said drape and coming into contact with the table surface, an extension sheet bonded along one edge of the said base sheet, said extension sheet overlapping at least approximately half its width over an end of said base sheet whereby a continuous and unbroken drape coverage is provided along the table to an operating surface, said extension sheet folded in a fan fold onto said base sheet and said base sheet folded into two fan fold groups from opposite edges of the sheet, one of said base sheet fan folds overlapping portion of the extension sheet fold, said one folded group then folded onto the second folded group to provide said compact package, whereby said fan fold groups are unfoldable from said compact package for first spreading the base sheet and subsequently unfolding said extension sheet.

* * * * *